United States Patent [19]

MacKenzie

[11] Patent Number: Plant 6,960

[45] Date of Patent: Aug. 1, 1989

[54] PERIWINKLE PLANT NAMED RALPH SHUGERT

[75] Inventor: David S. MacKenzie, Spring Lake, Mich.

[73] Assignee: Hortech, Spring Lake, Mich.

[21] Appl. No.: 217,421

[22] Filed: Jul. 11, 1988

[51] Int. Cl.[4] ..... A01H 5/00

[52] U.S. Cl. ..... Plt./54

[58] Field of Search ..... Plt./54

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A lesser periwinkle plant named Ralph Shugert, characterized by its glossy, reflexed foliage which is deep green and surrounded by thin white margins, and its large, deep violet, five-parted flowers.

2 Drawing Sheets

The present invention comprises a new and distinct cultivar of *Vinca minor,* hereafter referred to by the cultivar name Ralph Shugert.

Ralph Shugert is a new and distinct variety of lesser periwinkle, a suffrutiscent creeping vine similar to European and Western Asian ground covers. Ralph Shugert is outstanding for its very glossy, deep green foliage surrounded by thin white margins. It is characterized, in addition, by its large, deep-violet, five parted flowers.

Ralph Shugert originated as a branch sport of the cultivar *Vinca minor* Bowlesii — an all green leaved, large flowered cultivar. The first successful asexual reproduction of Ralph Shugert (named for a prominent American Horticulturist) was carried out by its discoverer, David S. Mackenzie. This propagation took place under controlled conditions at Hortech, Spring Lake, Mich., on Aug. 1, 1986.

The sport was excised and sectioned three times to create three leaf and node cuttings. Following treatment with the root promoting product "Rootone" and six weeks under intermittent mist, three rooted cuttings were transplanted for evaluation.

On Nov. 9, 1987 international registration as a woody plant cultivar was applied for. The International Registrar, at Longwood Gardens, Del., approved the application for registration on Nov. 16, 1987.

Ralph Shugert has not been observed under all possible environmental conditions, and the phenotype may vary significantly with variations in environment, such as temperature, light intensity and day length. The following observations, measurements and comparisons describe this plant as grown in Spring Lake, Mich. under greenhouse conditions that approximate those generally used in commercial practice.

BRIEF DESCRIPTION OF THE VARIOUS VIEWS OF THE DRAWING

Illustration 1 is a perspective view of Ralph Shugert.

Illustration 2 is a perspective view of Argento Variengata.

The accompanying photographic illustrations show typical foliage of the cultivar and the closest known comparison cultivar, with color being as accurate as possible with renditions of this type. The photographs were taken at 10:00 a.m. on a sunny autumn morning in Michigan. The film used was Kodakrome ISO 64, converted to Kodak prints. No filters were used.

The following traits have been repeatedly observed and are determined to be the basic characteristics of Ralph Shugert, which in combination distinguish this periwinkle as a new and distinct cultivar. The color codes correspond to The Royal Horticultural Society Colour Chart.

1. Stems of this cultivar arise at acute angles to the growing medium. These stems droop over and contact the medium as their weight increases during elongation. They then trail in a vine like fashion, with limited or no branching.
2. Typical stems are suffrutiscent (woody at the base and more herbaceous terminally), and are a uniformly colored medium green 147B. The stems are round, and have diameters of about 3/32 of an inch.
3. Internodes range in length from about 1 to 2 inches. The nodes are swollen and root after about 4 to 8 weeks of contact with the growing medium. Thereafter, the plants generate new shoots from their crowns.
4. Evergreen foliage is simple and arranged in opposite pairs. In youth, the foliage is irregularly crinkled and colored a medium green 141A with yellowish cream colored margins 145A. During maturation, the leaves enlarge and become smooth. The adult foliage is attached by long, light green 145A petioles of about ½ inch.
5. The leaf blades are reflexed, and range from 1 to 1½ inches in length by ¾ to 1 inch across. They are ovate shaped (occasionally tending toward oblong ovate); their apexes are acute to obtusish; and their bases are typically acute.
6. The midribs are prominent, elevated dorsally and light green in color 145B. Primary branches are elevated at obtuse angles to the basal ends of the midribs. They have the same dark green color 139A as the leaf centers. Leaf color is glossy deep green 139A. The white 157B margin is typically 1/32 inch wide and entire.
7. Bisexual solitary flowers are borne primarily in midspring and sporadically through the growing season on ½ inch long, light green 145B peduncles from the leaf axils.
8. The flowers are typically composed of calyxes of five, small, linear calyx lobes, which are light green in color 145C and ¼ inch long by ⅛ inch across. Often splotched medium green 141C centrally.
9. The corolla is more or less funnelform, 1 to 1⅜ inches in diameter, five lobed, and colored deep violet 90B.

10. The seldom observed fruit are pairs of elongate, light green 143C (to 1½ inches long) cylindrical follicles.

The only registered and most closely related cultivar is *Vinca minor* Argenteo-Variegata. It is variegated, like Ralph Shugert, but its leaves are flattish rather than reflexed. Its leaves are irregularly splotched in creamy white, which extends throughout the center of the leaves. The leaves of Ralph Shugert, however, are thinly edged in white. The flowers are also different;

namely pale lilac rather than deep violet, as in Ralph Shugert.

Propagation is successfully achieved by layering, cuttings (leaf node and stems) and crown division. No resistance to common diseases and pests of this host has, to date, been verified.

I claim:

1. A new and distinct lesser periwinkle plant named Ralph Shugert, as described and illustrated.

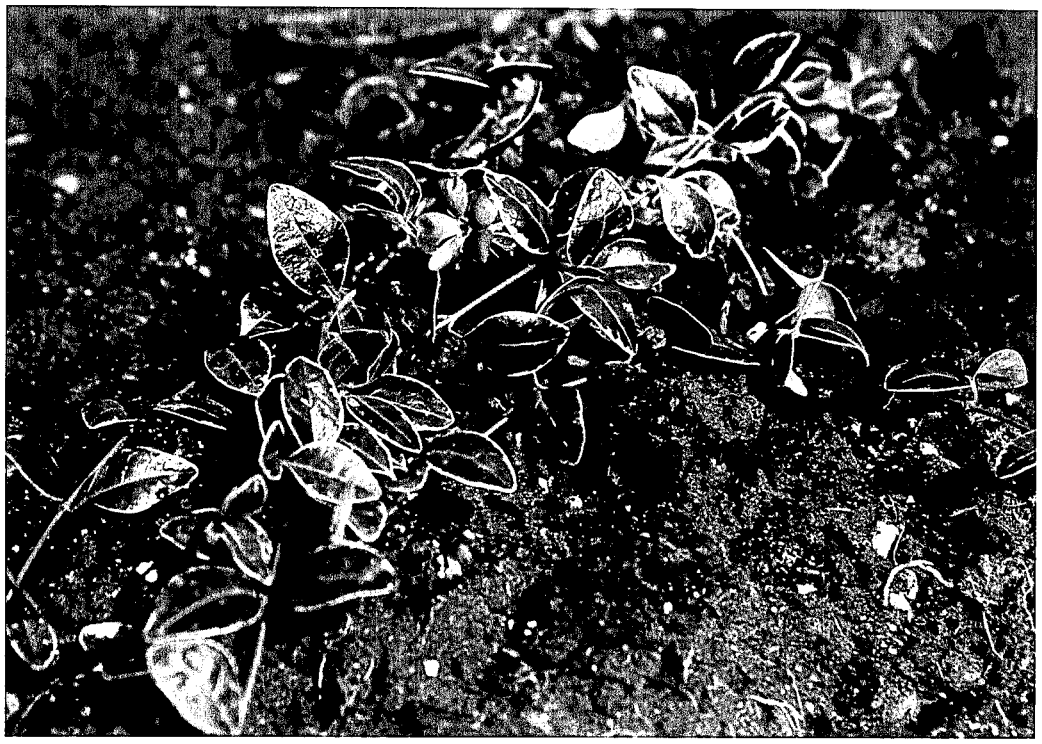

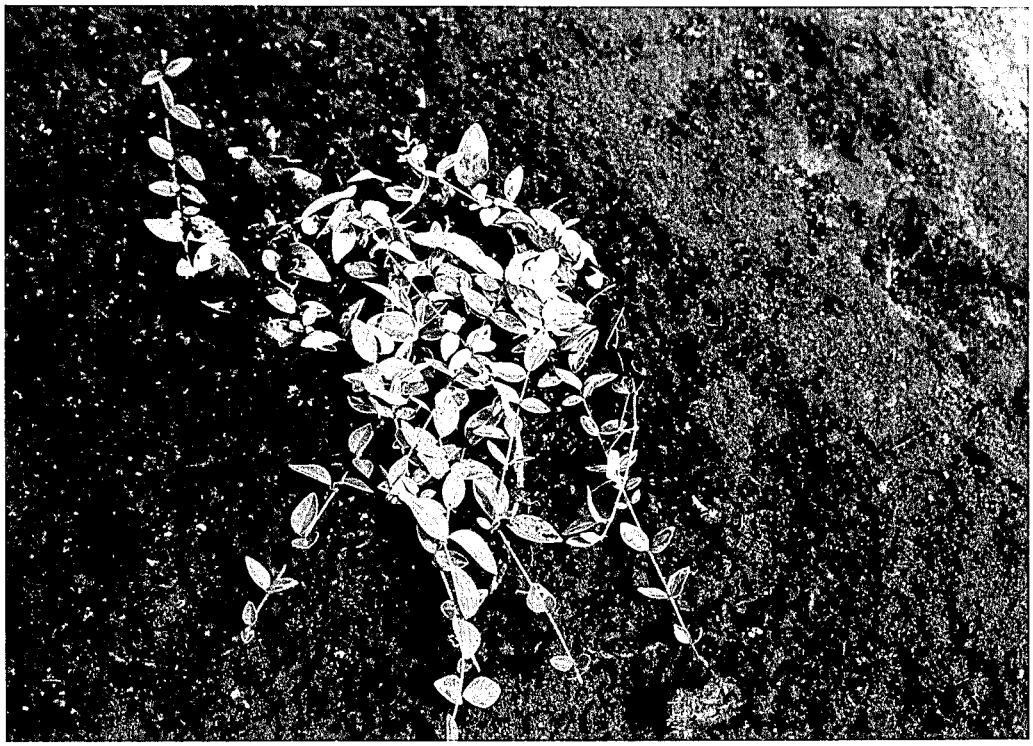

* * * * *